United States Patent [19]

Thompson et al.

[11] Patent Number: 5,467,636

[45] Date of Patent: Nov. 21, 1995

[54] FLAT PLATE SENSOR WITH A ROBUST PACKAGE DESIGN

[75] Inventors: David A. Thompson, Burton; Venkatesh Rajagopalan, Flint; Kurt W. Wright, Fenton; John J. Sterba, Clio; William J. Paulus; Nancy J. Paulus, both of Grand Blanc; Kathryn M. McCauley, Durand; David K. Chen, Rochester Hills, all of Mich.

[73] Assignee: General Motors Corporation, Detroit, Mich.

[21] Appl. No.: 313,689

[22] Filed: Sep. 27, 1994

[51] Int. Cl.⁶ .............................. G01N 27/12; B05D 5/12; H01C 7/00
[52] U.S. Cl. .............................. 73/23.31; 338/34; 422/98; 73/116; 123/672; 123/434
[58] Field of Search .............................. 73/23.31, 31.05, 73/31.06, 116, 117; 338/34

[56] References Cited

U.S. PATENT DOCUMENTS

| | | | |
|---|---|---|---|
| 4,130,797 | 12/1978 | Hattori et al. | 324/65 P |
| 4,214,472 | 7/1980 | Maxwell et al. | 73/23 |
| 4,236,138 | 11/1980 | Segawa et al. | 338/34 |
| 4,255,842 | 9/1980 | Schlesselman et al. | 338/34 |
| 4,308,518 | 12/1981 | Hattori et al. | 338/34 |
| 4,320,378 | 3/1982 | Taniguchi et al. | 338/34 |
| 4,403,207 | 9/1983 | Murphy et al. | 338/34 |
| 4,414,531 | 11/1983 | Novak | 338/34 |
| 4,535,316 | 8/1985 | Wertheimer et al. | 338/34 |
| 4,665,740 | 5/1987 | Matsumoto et al. | 73/116 |
| 4,668,477 | 5/1987 | Nishio et al. | 422/98 |
| 4,883,643 | 11/1989 | Nishio et al. | 422/94 |
| 4,958,514 | 9/1990 | Takami et al. | 73/25.03 |
| 5,031,445 | 7/1991 | Kato et al. | 73/23.31 |
| 5,039,972 | 8/1991 | Kato et al. | 338/34 |
| 5,182,136 | 1/1993 | Saburi et al. | 427/126.3 |
| 5,329,806 | 7/1994 | McClanahan et al. | 73/31.05 |

*Primary Examiner*—Hezron E. Williams
*Assistant Examiner*—J. David Wiggins
*Attorney, Agent, or Firm*—Cary W. Brooks

[57] ABSTRACT

The invention includes a flat plate exhaust sensor including a flat plate sensing element which is carried by a first ceramic insulator having at its upper end an upwardly extending annular ring. The annular ring defines a disc-shaped recess which is filled with a glass seal. Thus, the glass seal extends from the flat plate sensor to the annular ring of the ceramic insulator. The sensor includes an upper tubular shell which includes at the lower end a leg portion which extends inside an inner wall of a lower tubular shell. The leg portion includes a foot which is bent to match an outwardly extending sloped annular shoulder formed on an upper insulator. The upper insulator is seated on the glass seal. An intermediate gasket is formed by an active metal braze gasket between the foot and the outwardly extending sloped annular shoulder of the upper insulator. An external seal is provided by a braze ring which joins an upper end of the lower tubular shell to the upper tubular shell. The system removed the thermal expansion mismatch problems of prior art glass seal sensors.

4 Claims, 3 Drawing Sheets

FLAT PLATE SENSOR WITH A ROBUST PACKAGE DESIGN

FIELD OF THE INVENTION

The invention relates to flat plate sensors, and more particularly to flat plate automotive exhaust sensors with a unique package design.

BACKGROUND OF THE INVENTION

FIG. 1 illustrates a flat plate automotive exhaust sensor of the prior art. The exhaust sensor includes a heated flat plate sensing element 138 which is carried in a tubular housing 116 and held in position by a first cement composition 140, glass seal 142 and a second cement composition 144, each of which extends from the flat plate heating element to the tubular wall 116 of the sensor. The heated flat plate sensing element includes an air reference channel formed therein and is positioned within the sensor to provide communication with an air source in the upper portion of the sensor. A glass seal prevents exhaust gas from travelling from the lower end of the sensor through the tubular housing and into the upper portion of the sensor to contaminate the air in the air reference channel of the sensing element. Glass seals are desirable because they are easily formed by firing glass frit in a furnace. Such sensors are used to monitor constituents in an automotive combustion engine exhaust gas stream such as oxygen, and to adjust the operation of the engine including the air/fuel ratio.

However, the glass seal, heated flat plate sensing element and the tubular shell have different thermal coefficients of expansion. When the sensor is exposed to high temperatures associated with combustion engine exhaust, the glass seal, heated flat plate sensing element and the tubular shell expand and contract at different rates. This often results in leakage paths between the glass seal and the tubular shell, thereby contaminating the air reference with exhaust gases.

The present invention overcomes many of the deficiencies of the prior art sensors.

SUMMARY OF THE INVENTION

The invention includes a flat plate exhaust sensor including a flat plate sensing element which is carried by a first ceramic insulator having an upwardly extending annular ring at the upper end and outer edge of the first ceramic insulator. The annular ring defines a recess which is filled with a glass seal. Thus, the glass seal extends from the flat plate sensor to the annular ring of the ceramic insulator. The sensor includes an upper tubular shell which includes a leg portion which extends inside the lower tubular shell. The leg portion includes a foot which is bent to match an outwardly extending sloped annular shoulder formed on a second insulator. The second insulator is seated on the glass seal. An intermediate gasket is formed by an active metal braze gasket between the foot and the outwardly extending sloped annular shoulder of the second insulator. An external seal is provided by a braze ring which joins an upper end of the lower tubular shell to the upper tubular shell. The system provides a robust flat plate sensor design that removes the problems associated with glass seals.

These and other objects, features and advantages of the present invention will become apparent from the following brief description of the drawings, detailed description and appended claims and drawings.

DETAILED DESCRIPTION

Figure 2:
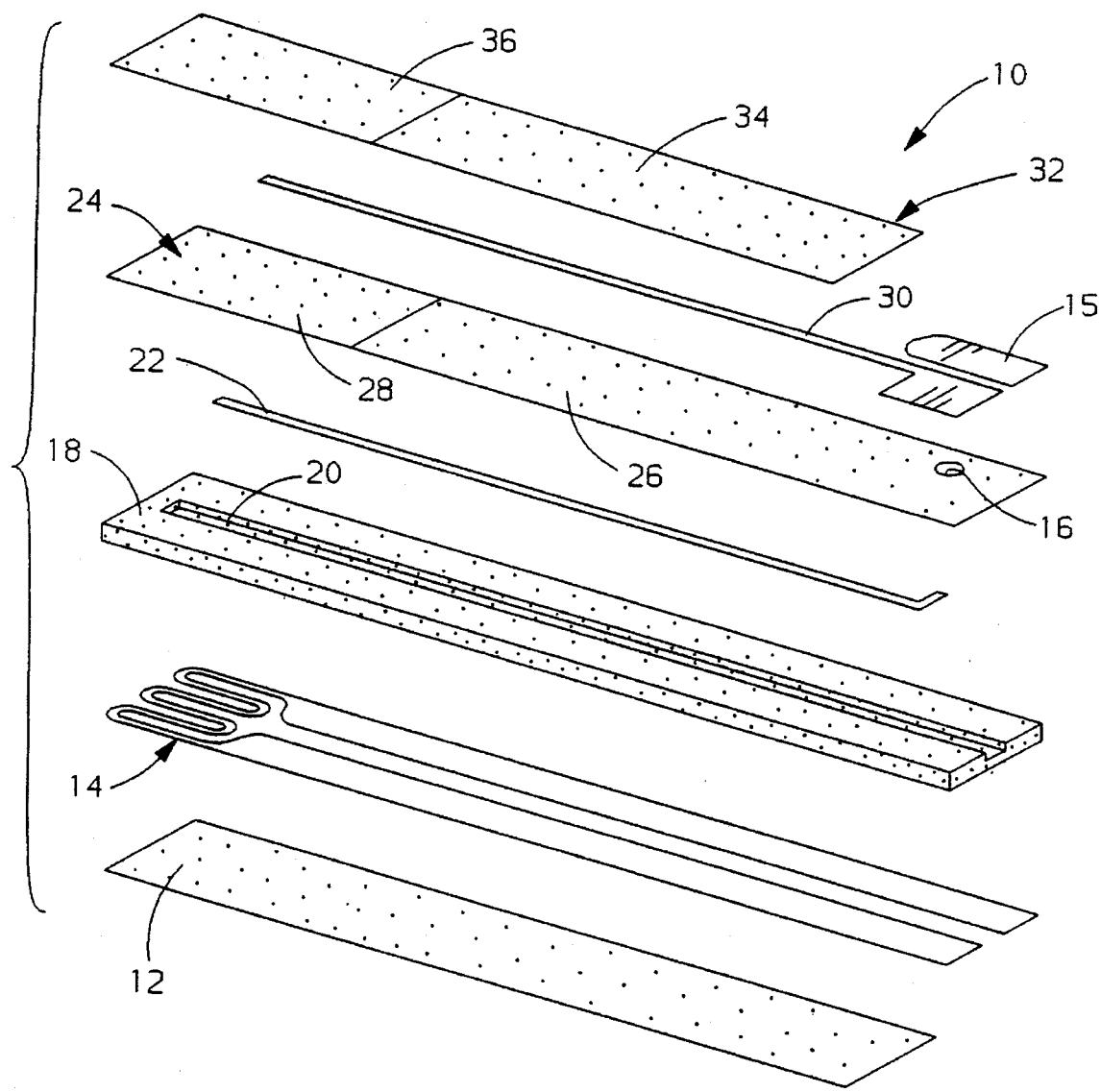
FIG. 2 illustrates a flat plate sensing element for the present invention.

FIG. 2 illustrates an exhaust sensor 10 according to the present invention including, an overlapping relationship, the following elements: a heater dielectric protective tape 12; a printed heater 14; an alumina substrate 18 including an air reference channel 20 formed therein; an inner electrode 22 printed on one side of a co-cast composite tape 24 including a dielectric portion 26 and an electrolyte body portion 28; an outer electrode 30 and sensor pads printed on the other side of the co-cast composite tape; and a protective outer tape 32 including a dense alumina portion 34 and a porous alumina portion 36 overlying the electrolyte body portion 28 of the composite tape 32. The tape 24 has a hole 16 formed therein to provide contact between pad 15 and inner electrode 22. The co-cast composite tape 24 includes a first portion 26 which is a dielectric material such as alumina and the second portion 28 is a porous electrolyte material such as zirconia near one end of the sensing element. The co-cast composite tape may be made from a variety of methods such as slurry casting, roll compaction or calendaring. Such processes are disclosed in U.S. patent application Ser. No. 08/196,863 filed Feb. 15, 1994 assigned to the assignee of the present invention, the disclosure of which is hereby incorporated by reference. The various layers of the sensing element are fired together to form a single flat plate sensing element.

Figure 3:
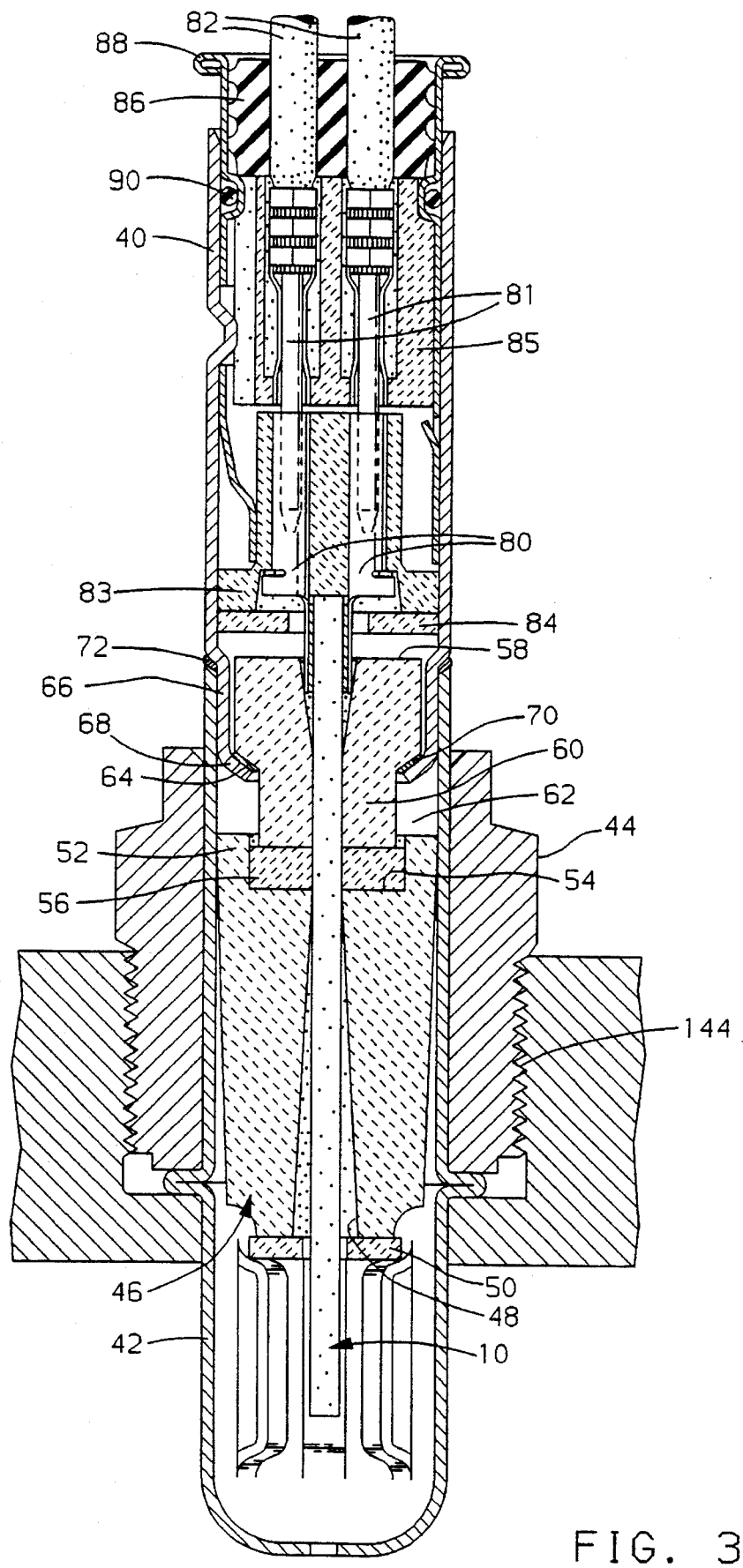
FIG. 3 illustrates a flat plate sensor according to the present invention.

The sensor according to the present invention includes a flat plate element as illustrated in FIG. 2 and described above. As shown in FIG. 3, the flat plate element 10 is carried in a sensor housing having an upper tubular shell 40, a lower tubular shell 42, a threaded fitting 44 surrounding the lower tubular shell. A first (lower) ceramic insulator 46 is carried in the lower tubular shell 42 and has a hole 48 extending therethrough for receiving the flat plate sensor element 10. The first ceramic insulator is held in position by a glass preform 50. The flat plate element extends through the ceramic insulator and extends outwardly from both ends of the insulator. The upper end of the insulator includes a upwardly extending annular ring 52 at the outer edge of the insulator and a flat shoulder 54 which together define a disc-shaped recess. A glass seal 56 is provided in the recess. The glass seal extends from the flat plate element 10 to the upwardly extending annular ring 52 of the first ceramic insulator. A suitable glass seal is prepared from glass frit material which is available from Ferro Corp. Preferably, the glass seal 56 has a thickness of about 0.01 to about 0.03 inches.

A second (upper) ceramic insulator 58 is seated on the glass seal and has a hole formed therein for receiving the flat plate element. The second ceramic insulator includes a lower portion 60 which has a width equal to or less than the width of the recess formed in the first ceramic insulator. Thus, a gap 62 exists between the lower end of the second ceramic insulator and the lower tubular shell 42. The second ceramic insulator also includes an upper portion having an outwardly extending sloped annular shoulder 64.

The lower end of the upper tubular shell includes a leg portion 66 which is bent to extend inside an inner wall of the lower tubular shell 42. The leg portion also includes a foot 68 which is bent to be parallel with the outwardly extending sloped annular shoulder 64 of the second ceramic insulator. The foot 68 and the second ceramic insulator are held together in a fixed position by an active metal braze gasket 70. The braze gasket is formed from an active metal braze material which includes silver, copper and titanium, which preferably are present in 59%, 40% and 1% by weight, respectively. A suitable active metal braze material is available from Lucas Milhaupt Inc. company under the trade mark BR559™.

A braze ring 72 is formed at the upper end of the lower tubular shell 42 to join the lower tubular shell to the upper tubular shell 40. The braze ring 72 may be made from a filler material such as silver and copper. Preferably the braze ring material is made from BR559™.

The sensor also includes electrical connectors 80 communicating with the flat plate sensing element 10, and a second set of electrical connectors 81 and wires 82 to provide electricity from an external source. The electrical connectors 80 are held in position by an adapter 83 and connectors 81 held by adapter 85. Both adapter 81, 85 may be steatite. A glass seal 84 caps the upper portion of the sensing element. The wires extend through a Teflon seal 86 held by a connector 88 frictionally secured in the upper shell 40 by an O-ring 90.

Figure 1:
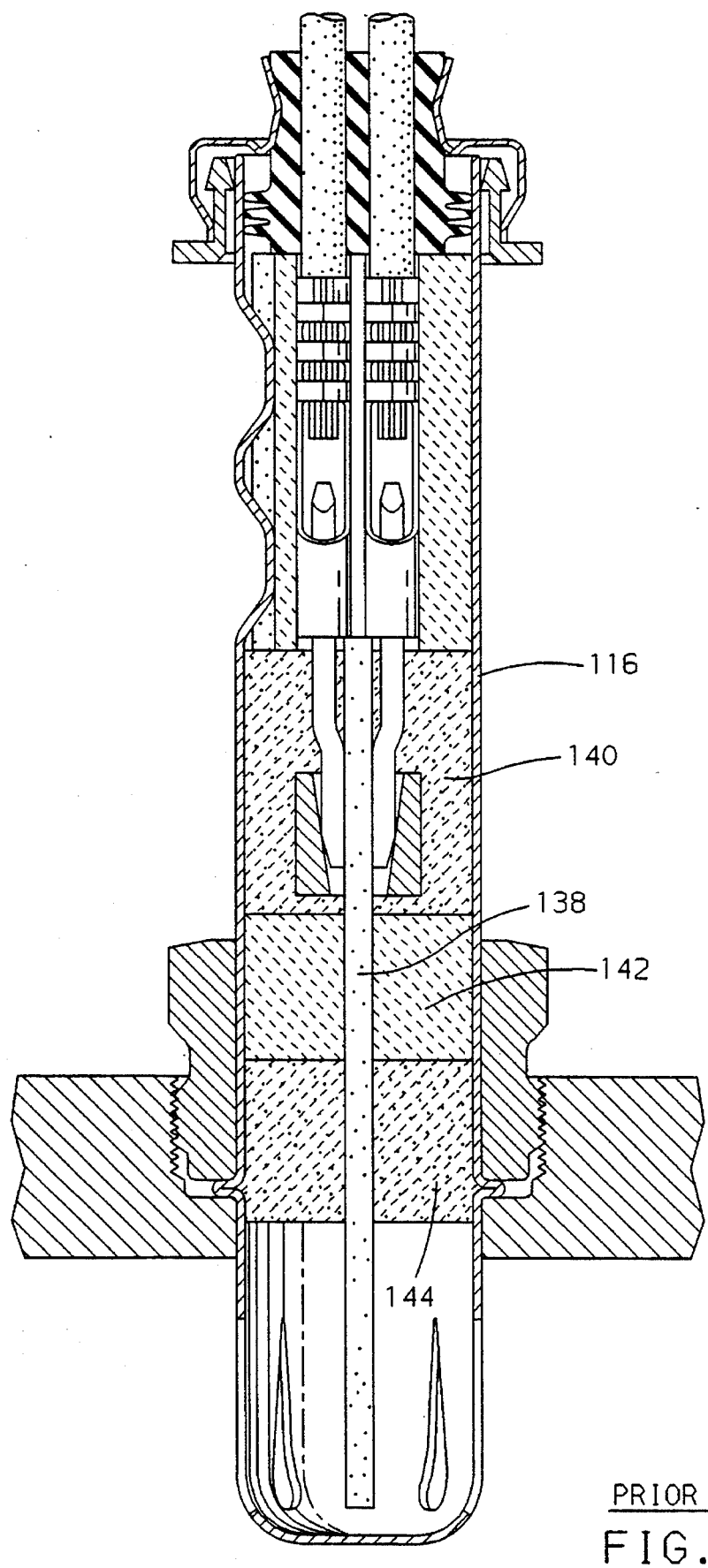
FIG. 1 illustrates a prior art flat plate oxygen sensor.

As can be seen by comparing FIGS. 1 and 3, the present invention does not utilize a single sealing system of the prior art. Instead, the present invention utilizes separate internal, intermediate and external seals. The internal seal is formed by the glass seal 56 held in the annular recess in the lower ceramic insulator. The intermediate seal is formed by the active metal braze gasket 70 connecting the foot 68 of the upper tubular shell to the shoulder formed on the second ceramic insulator. The external seal is formed by the braze ring 72 which joins the upper and lower tubular shells. The use of three separate seals overcomes the problems associated with the prior art single glass seal systems. In the present invention, the glass seal does not extend all the way from the flat plate element to the tubular shell. As such, the internal glass seal is positioned such that it is in contact with the flat plate sensor element and the first ceramic insulator. The ceramic insulator has a much closer thermal coefficient of expansion to the glass seal than does the metal tubular shell. Even if there is a leak formed around the external metal-to-metal braze seal (part 72 of exhaust gas sensor 10 in FIG. 3), exhaust gas cannot reach the air reference channel (part 20 of flat plate sensing element in FIG. 2) because of the intermediate braze gasket (part 70 of exhaust gas sensor 10 in FIG. 3). Thus, the present invention overcomes disadvantages associated with prior art glass seal sensor systems.

The embodiments of the invention in which an exclusive property or privilege is claimed is defined as follows in the appended claims; whereby we claim:

1. An automotive exhaust sensor comprising:

an upper and lower tubular metal shell joined together with an airtight seal;

a first ceramic insulator carried in the lower tubular shell having a slot-shaped hole formed therein for receiving a length-wise portion of a flat plate sensing element, said first ceramic insulator including an upper end having an upwardly extending annular ring immediately adjacent the walls of the lower tubular shell, said upwardly extending annular ring defining a recess on the top central portion of the first ceramic insulator;

a flat plate element received in the first ceramic insulator and extending above the annular ring;

a glass seal formed in the recess as an internal seal and extending radially outward from the flat plate sensing element to the annular ring of said first ceramic insulator.

2. An automotive exhaust sensor as set forth in claim 1 further comprising a second ceramic insulator seated on the glass seal and having a lower end having a width less than the inside diameter of the lower tubular shell, said second ceramic insulator having an outwardly extending sloped annular shoulder formed above the lower end of the second ceramic insulator, said second ceramic insulator having a slot-shaped hole formed therethrough for receiving a lengthwise portion of the flat plate sensing element inserted therein;

said upper tubular shell having a annular leg portion extending inside of the lower tubular shell, said leg portion having a inwardly extending sloped foot bent to match the outwardly extending sloped annular shoulder of the second ceramic insulator; and an active metal braze gasket formed between the foot and the annular shoulder of the second ceramic insulator as an intermediate seal.

3. An automotive exhaust sensor as set forth in claim 2 wherein said active metal braze gasket is formed from a material comprising silver, copper and titanium.

4. An automotive exhaust sensor as set forth in claim 3 where said silver, copper and titanium are present in about 59%, 40% and 1% by weight respectively.

\* \* \* \* \*